US008815035B2

(12) United States Patent
Schneider

(10) Patent No.: US 8,815,035 B2
(45) Date of Patent: Aug. 26, 2014

(54) APPARATUSES AND METHODS FOR FABRICATING ELASTOMERIC LAMINATES

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/057,510

(22) Filed: Oct. 18, 2013

(65) Prior Publication Data

US 2014/0041797 A1 Feb. 13, 2014

Related U.S. Application Data

(62) Division of application No. 13/366,435, filed on Feb. 6, 2012, now Pat. No. 8,585,849.

(51) Int. Cl.
*A61F 13/15* (2006.01)

(52) U.S. Cl.
USPC .................. 156/163; 156/229; 156/495

(58) Field of Classification Search
CPC .............. A61F 13/15699; A61F 13/15609; A61F 13/49011; A61F 13/15601; A61F 13/49009; A61F 13/15585; A61F 13/539; A61F 13/51478; A61F 2013/51429; A61F 13/15764; A61F 13/15593; B65H 20/00
USPC .......... 156/161, 163, 160, 180, 229, 494, 495; 229/17, 29, 30, 42, 152
See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,167,897 A | 12/1992 | Weber et al. |
| 5,360,420 A | 11/1994 | Cook et al. |
| 5,562,646 A | 10/1996 | Goldman et al. |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |

(Continued)

FOREIGN PATENT DOCUMENTS

WO WO 2011/025032 A1 3/2011

OTHER PUBLICATIONS

12342 International Search Report, dated May 13, 2013, 8 pages.

*Primary Examiner* — Katarzyna Wyrozebski Lee
*Assistant Examiner* — Vishal I Patel
(74) *Attorney, Agent, or Firm* — Charles R. Matson

(57) ABSTRACT

The present disclosure relates to methods for manufacturing absorbent articles, and in particular, to methods for making elastomeric laminates that may be used as components of absorbent articles. And the methods and apparatuses according to the present disclosure may be configured to automatically rethread elastic materials that may break during the assembly process.

11 Claims, 17 Drawing Sheets

(56) References Cited

U.S. PATENT DOCUMENTS

| | | | |
|---|---|---|---|
| 5,916,661 A | 6/1999 | Benson et al. | |
| 5,968,025 A | 10/1999 | Roe et al. | |
| 6,057,024 A * | 5/2000 | Mleziva et al. | 428/114 |
| 6,107,537 A | 8/2000 | Elder et al. | |
| 6,107,539 A | 8/2000 | Palumbo et al. | |
| 6,118,041 A | 9/2000 | Roe et al. | |
| 6,153,209 A | 11/2000 | Vega et al. | |
| 6,410,129 B2 | 6/2002 | Zhang et al. | |
| 6,426,444 B2 | 7/2002 | Roe et al. | |
| 6,545,197 B1 | 4/2003 | Muller et al. | |
| 6,586,652 B1 | 7/2003 | Roe et al. | |
| 6,617,016 B2 | 9/2003 | Zhang et al. | |
| 6,627,787 B1 | 9/2003 | Roe et al. | |
| 6,790,798 B1 | 9/2004 | Suzuki et al. | |
| 6,825,393 B2 | 11/2004 | Roe et al. | |
| 6,861,571 B1 | 3/2005 | Roe et al. | |
| 7,222,654 B2 | 5/2007 | Schneider et al. | |
| 7,513,969 B2 * | 4/2009 | Ashraf | 156/163 |
| 7,569,039 B2 | 8/2009 | Matsuda et al. | |
| 2003/0075029 A1 | 4/2003 | Franklin et al. | |
| 2004/0005832 A1 * | 1/2004 | Neculescu et al. | 442/149 |
| 2004/0068246 A1 | 4/2004 | Rose et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2005/0241773 A1 | 11/2005 | Schneider et al. | |
| 2007/0131343 A1 | 6/2007 | Nordang | |
| 2009/0312730 A1 | 12/2009 | Lam et al. | |
| 2010/0193135 A1 | 8/2010 | Eckstein et al. | |
| 2012/0061015 A1 | 3/2012 | LaVon et al. | |
| 2012/0061016 A1 | 3/2012 | LaVon et al. | |

* cited by examiner

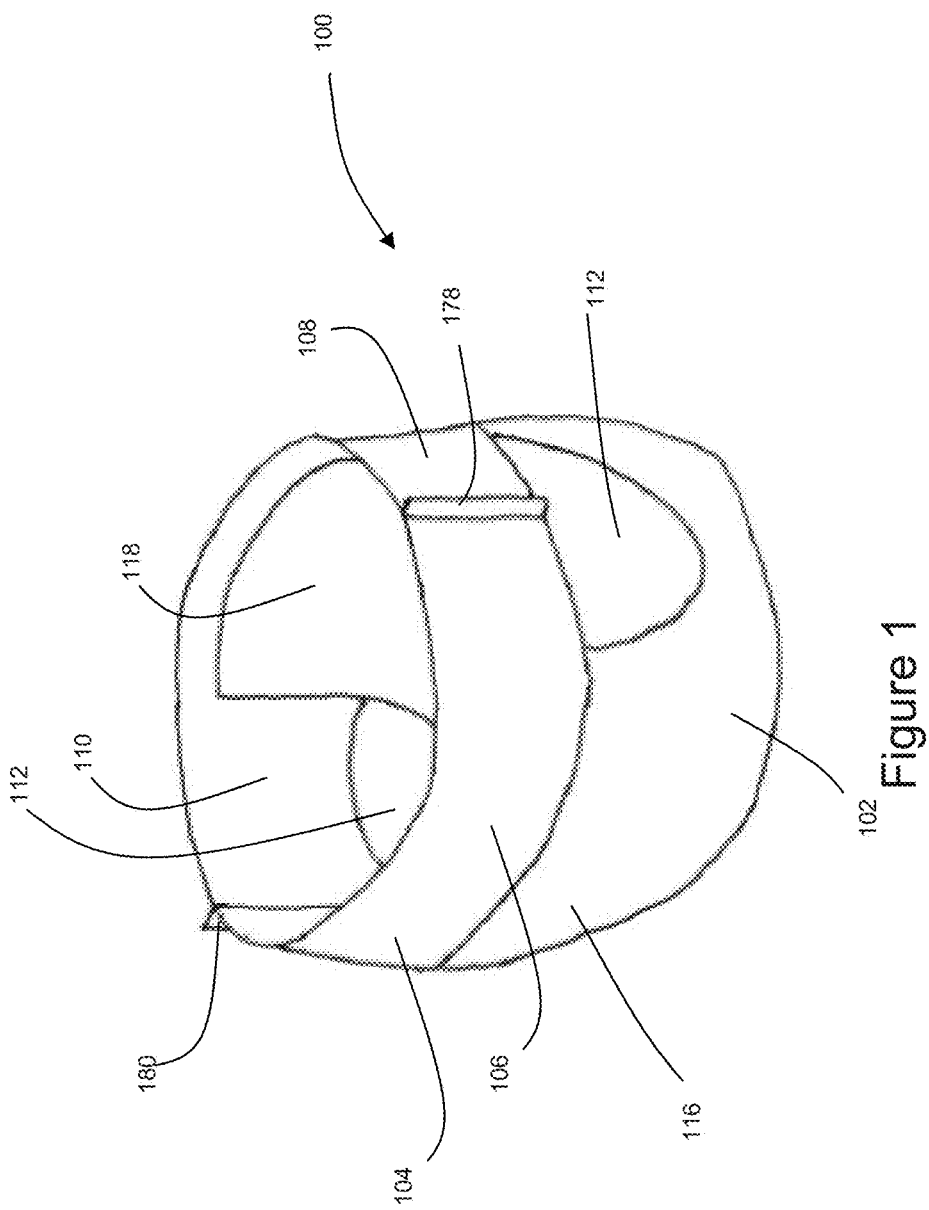

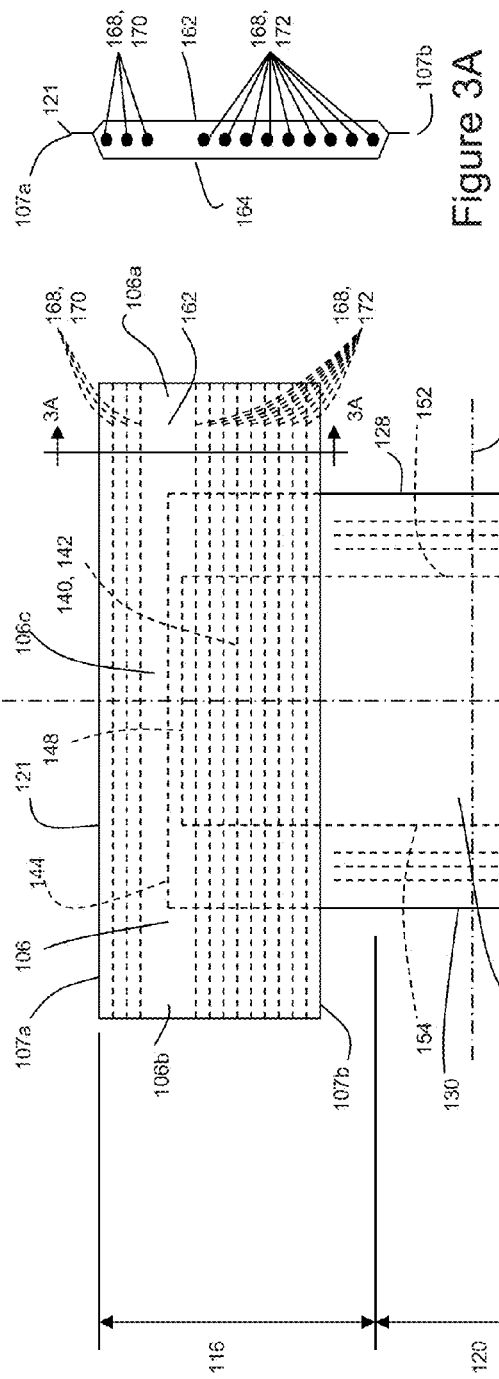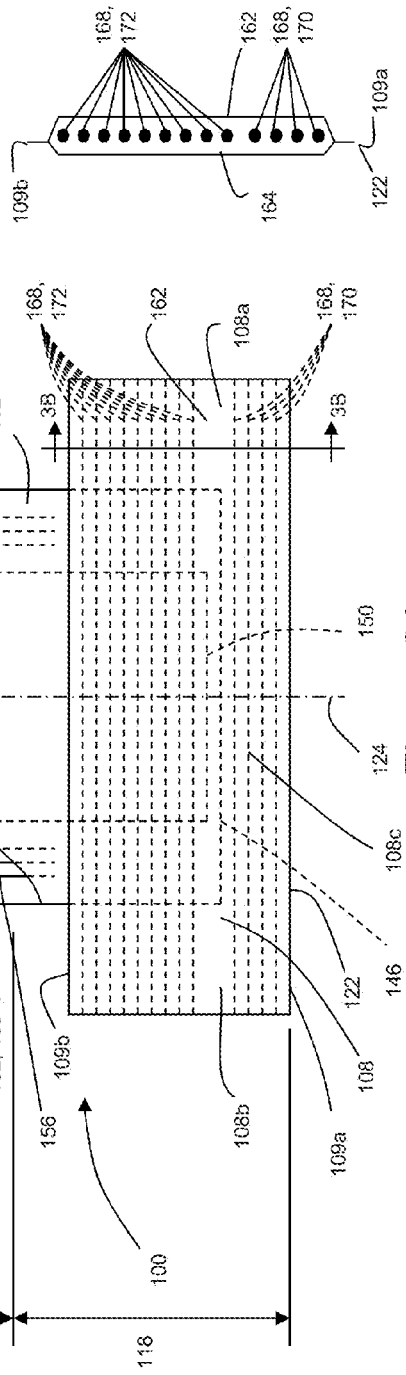

APPARATUSES AND METHODS FOR FABRICATING ELASTOMERIC LAMINATES

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands forming corrugations. The resulting elastomeric laminate is stretchable to the extent that the corrugations allow the elastic strands to elongate.

During the manufacture of elastic laminates, problems can be encountered in the manufacturing process when bonding elastic strands to substrates. For example, tensioned elastic strands may break during the assembly process. If a strand breaks under tension, a loose end of the strand may tend to snap back a significant distance toward an upstream portion of the manufacturing process. As such, the loose end may become entangled in other upstream manufacturing components, which in turn, may necessitate stopping the process in order to properly rethread the elastic strand to the intended position on the production machinery.

Consequently, it would be beneficial to provide a method and apparatus for producing an elastomeric laminate that is capable of automatically capturing and rethreading elastic material that breaks during the production process.

SUMMARY OF THE INVENTION

The present disclosure relates to methods for manufacturing absorbent articles, and in particular, to methods for making elastomeric laminates that may be used as components of absorbent articles. And the methods and apparatuses according to the present disclosure may be configured to automatically rethread elastic materials that may break during the assembly process.

In one form, a method for making an elastomeric laminate includes the steps of: rotating a first roller about a first axis of rotation, the first roller having an outer circumferential surface having a surface speed $V1$; rotating a second roller about a second axis of rotation, the second roller having an outer circumferential surface having a surface speed $V1$, wherein the first roller and the second roller rotate in opposite directions, and wherein the first roller is adjacent the second roller to define a first nip between the first roller and the second roller; rotating a third roller about a third axis of rotation, the third roller having an outer circumferential surface having a surface speed $V2$, wherein $V2$ is greater than $V1$; supplying a first substrate having a first surface and an opposing second surface; continuously advancing the first substrate at speed $V2$ in a machine direction, wherein the first surface of the first substrate travels in an opposing direction to and in contact with the outer circumferential surface of the second roller, and wherein the second surface of the first substrate travels in the same direction as and in contact with the outer circumferential surface of the third roller; stretching an elastic material in the machine direction by advancing the elastic material through the first nip to the third roller; and joining the elastic material with the first surface of the first substrate while the second surface of the first substrate contacts the outer circumferential surface of the third roller.

In another form, a method for making an elastomeric laminate includes the steps of: rotating a first roller about a first axis of rotation, the first roller having an outer circumferential surface having a surface speed $V1$; rotating a second roller about a second axis of rotation, the second roller having an outer circumferential surface having a surface speed $V1$, wherein the first roller and the second roller rotate in opposite directions, and wherein the first roller is adjacent the second roller to define a first nip between the first roller and the second roller; rotating a third roller about a third axis of rotation, the third roller having an outer circumferential surface having a surface speed $V2$, wherein $V2$ is greater than $V1$; supplying a first substrate having a first surface and an opposing second surface; continuously advancing the first substrate at speed $V2$ in a machine direction, wherein the first surface of the first substrate travels in an opposing direction to and in contact with the outer circumferential surface of the second roller, and wherein the second surface of the first substrate travels in the same direction as and in contact with the outer circumferential surface of the third roller; advancing an elastic material in the machine direction through the first nip and to the third roller; stretching the elastic material in the machine direction between the first nip and to the third roller; separating the elastic material in the machine direction between the first nip and the third roller to create an upstream end portion and a downstream end portion; joining the upstream end portion of the elastic material with the first surface of the first substrate; and restretching the elastic material by conveying the upstream end portion of the elastic material with the first surface of the first substrate past the third roller.

BRIEF DESCRIPTION OF THE DRAWINGS

FIG. 1 is a perspective view of a diaper pant.

FIG. 2A is a partially cut away plan view of the diaper pant shown in FIG. 1.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 4AA is a schematic side view of a second embodiment of a converting apparatus adapted to manufacture an elastic laminate including a first substrate, a second substrate, and an elastic strand.

FIG. 4AB is a schematic side view of a third embodiment of a converting apparatus adapted to manufacture an elastic laminate including a first substrate, a second substrate, and an elastic strand.

DETAILED DESCRIPTION OF THE INVENTION

Figure 2B:
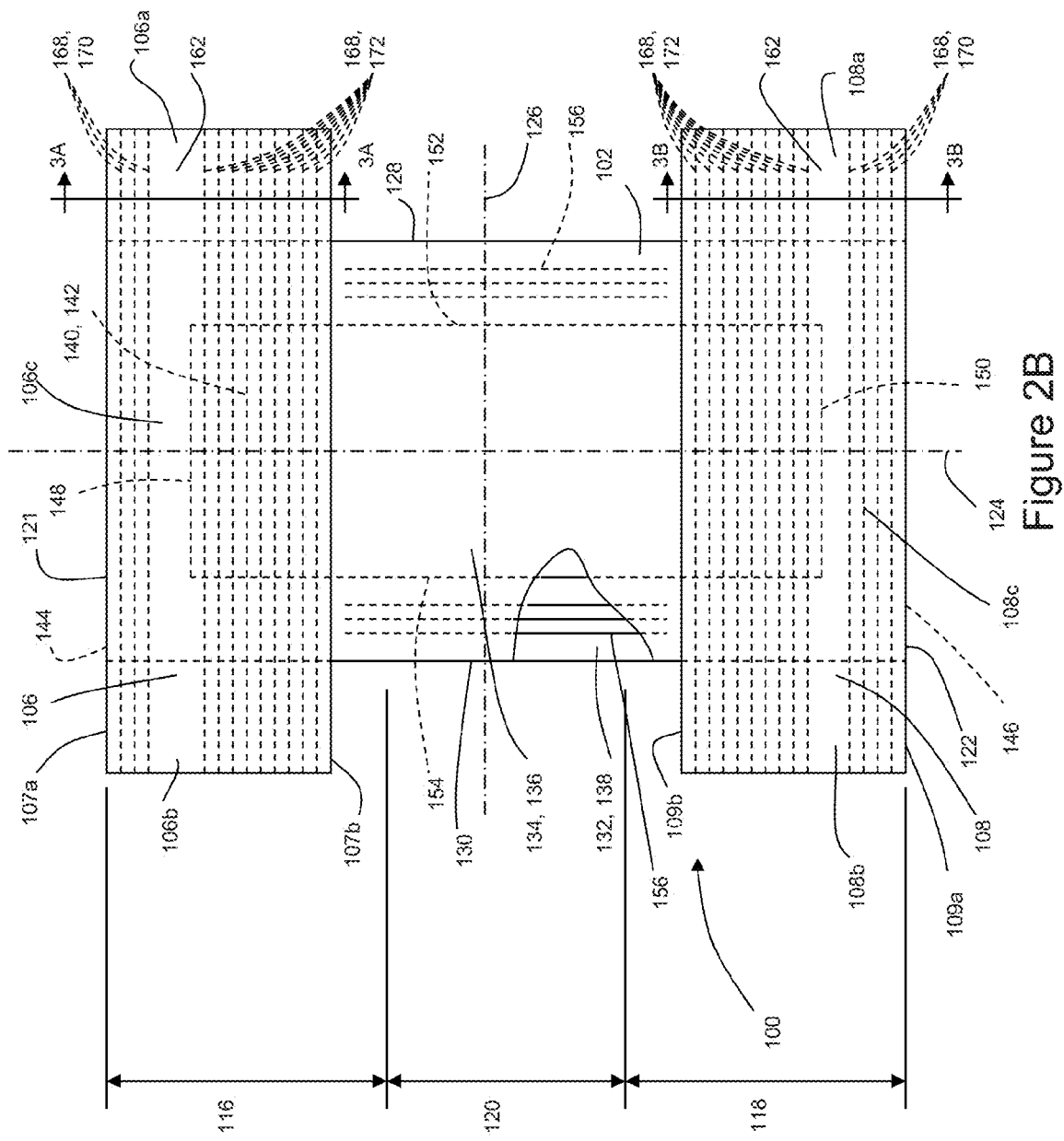
FIG. 2B is a partially cut away plan view of a second embodiment of a diaper pant.

The following term explanations may be useful in understanding the present disclosure: "Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The present disclosure relates to methods for manufacturing absorbent articles, and in particular, to methods for making elastomeric laminates that may be used as components of absorbent articles. The elastomeric laminates may include a first substrate, a substrate, and an elastic material located between the first substrate and second substrate. During the process of making the elastomeric laminate, the elastic material may be advanced and stretched in a machine direction and may be joined with either or both the first and second substrates advancing the machine direction. The methods and apparatuses according to the present disclosure may be configured to automatically rethread elastic materials that may break during the assembly process. As discussed in more detail below, the apparatuses may include metering devices arranged along a process machine direction, wherein the metering devices may be configured to stretch the advancing elastic material and/or join stretch elastic material with one or more advancing substrates. In the event that the stretched elastic material breaks before being joined with a substrate, the apparatuses continuously advances substrates and elastic materials from upstream metering devices to downstream metering devices. The apparatuses also automatically guide the loose end of the broken elastic material to a downstream metering device, which in turn, reestablishes the stretched condition of the elastic material, without having to stop the manufacturing process.

As previously mentioned, the elastomeric laminates made according to the processes and apparatuses discussed herein may be used as to construct various types of components used in the manufacture of different types of absorbent articles. To help provide additional context to the subsequent discussion of the process embodiments, the following provides a general description of absorbent articles in the form of diapers that include components including the elastomeric laminates that may be produced with the methods and apparatuses disclosed herein.

FIGS. 1 and 2A show an example of a diaper pant 100 that may include components constructed from elastomeric laminates assembled in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136.

The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. patent application Ser. No. 12/434,984.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 116 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 side panels may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

It is to be appreciated that various embodiments of diaper pants can be manufactured according the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011, which are all hereby incorporated by reference herein.

As previously mentioned, apparatuses and methods according to the present disclosure may be utilized to produce elastomeric laminates that may be used to construct various components of diapers 100, such as elastic belts, leg cuffs, and the like. For example, FIGS. 4A-6 show schematic views of converting apparatuses 300 adapted to manufacture elastomeric laminates 302. As described in more detail below, the converting apparatuses 300 shown in FIGS. 4A-6 operates to advance a continuous length of elastic material 304, a continuous length of a first substrate 306, and a continuous length of a second substrate 308 along a machine direction MD. The apparatus 300 stretches the elastic material 304 and joins the stretched elastic material 304 with the first and second substrates 306, 308 to produce an elastomeric laminate 302. It is to be appreciated that the elastic material 304 may include one or more continuous lengths of elastic strands, ribbons, and/or films.

The elastomeric laminates 302 can be used to construct various types of diaper components. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may used to construct waistbands in taped diaper configurations. Example taped diapers are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571. In yet other examples, the elastomeric laminates may be used to construct various types of leg cuff and/or topsheet configurations.

As discussed in more detail below, the apparatuses 300 may include metering devices arranged along a process machine direction, wherein the metering devices may be configured to stretch the advancing elastic material and/or join stretch elastic material with one or more advancing substrates. In the event that the stretched elastic material breaks before being joined with a substrate, the apparatuses continuously advances substrates and elastic materials from upstream metering devices to downstream metering devices. The apparatuses also automatically guide the loose end of the broken elastic material to a downstream metering device, which in turn, reestablishes the stretched condition of the elastic material, without the necessity of having to stop the manufacturing process.

Figure 4A:
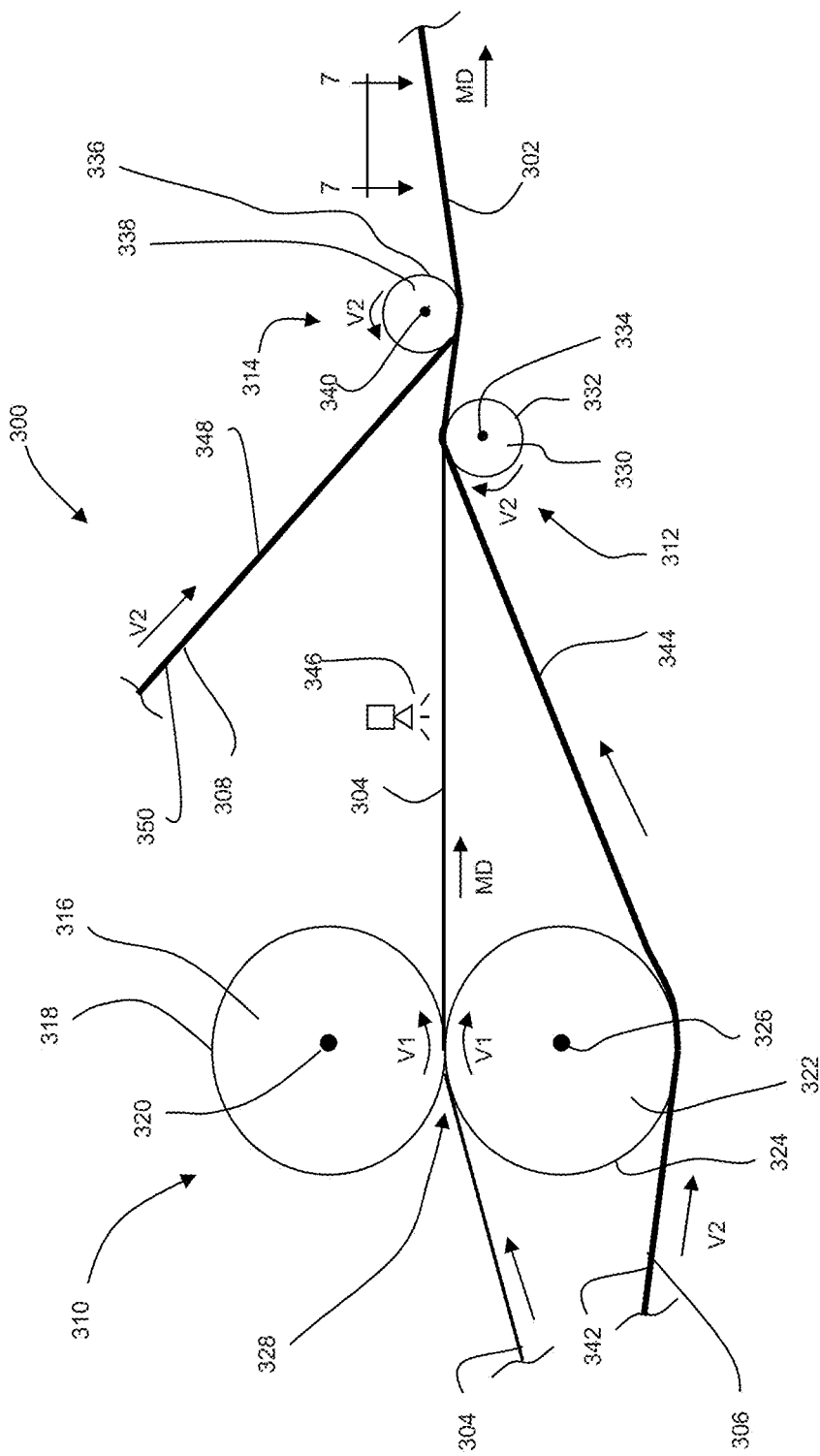
FIG. 4A is a schematic side view of a converting apparatus adapted to manufacture an elastic laminate including a first substrate, a second substrate, and an elastic strand.
Figure 6:
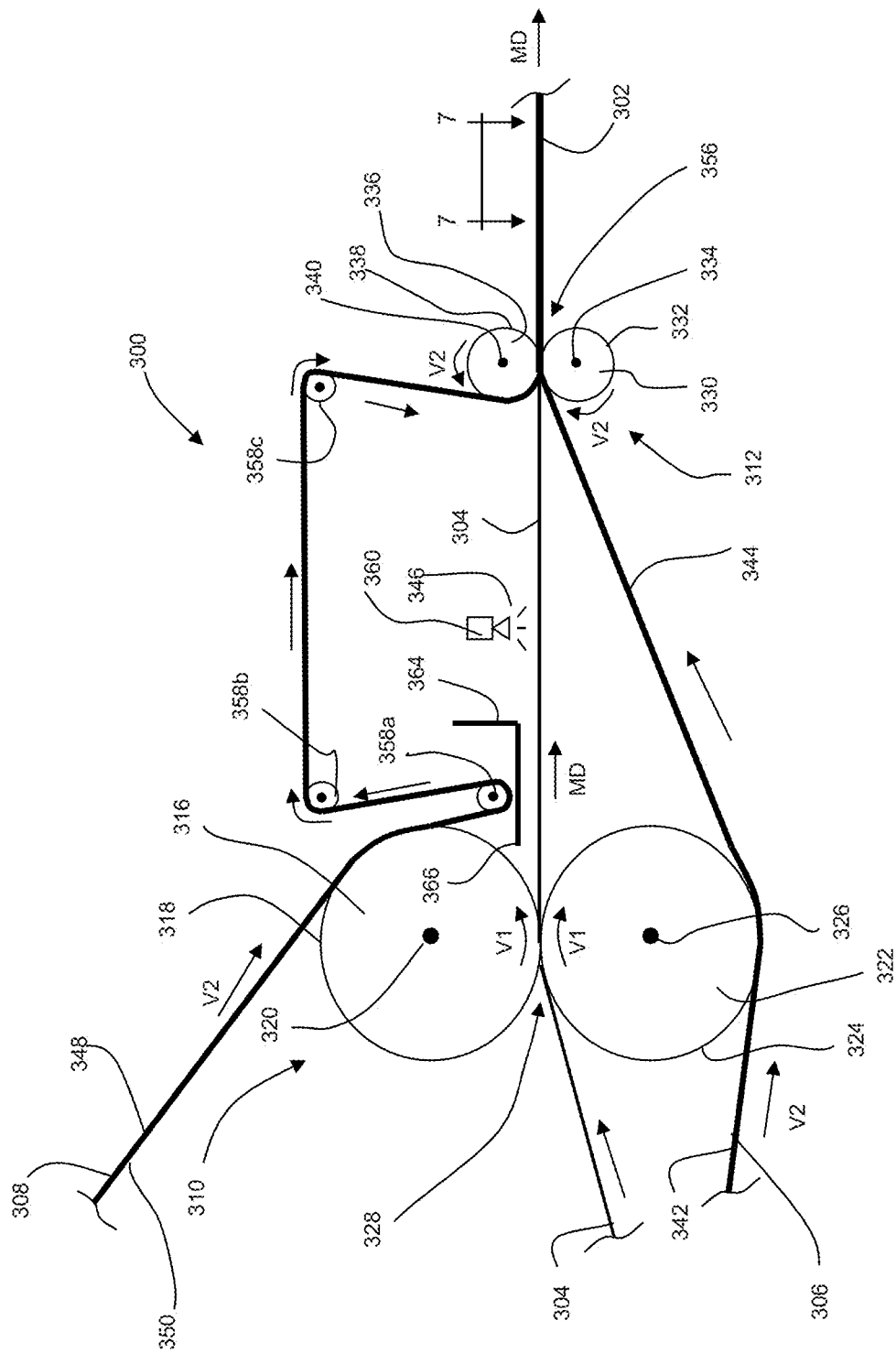
FIG. 6 is a schematic side view of a fifth embodiment converting apparatus including a shield and adapted to manufacture an elastic laminate including a first substrate, a second substrate, and an elastic strand.
Figure 7:
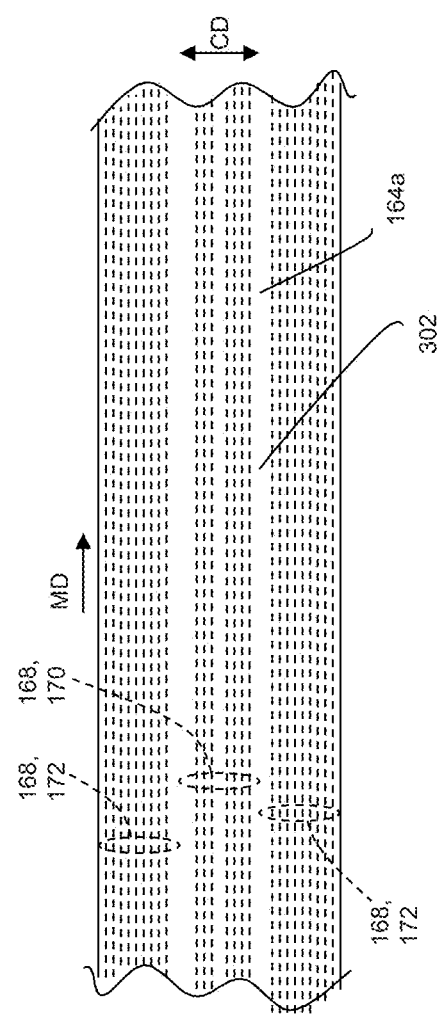
FIG. 7 is a view of an example continuous length of an elastomeric laminate from FIGS. 4A, 5A, and 6 taken along line 7-7.

As shown in FIG. 4A, the apparatus 300 includes a first metering device 310, a second metering device 312, and a third metering device 314. The elastic material 304 advances in the machine direction MD from the first metering device 310 to the second metering device 312. The first and second metering devices 310, 312 also operate to stretch elastic material 304 along the machine direction MD between the first and second metering devices 310, 312. The stretched elastic material 304 is joined with the first substrate 306 at the second metering device 312. And from the second metering device 312, the stretched elastic material 304 and first substrate 306 advance to the third metering device 314 and are joined with the second substrate 308 to produce an elastomeric laminate 302. FIG. 7 shows a view of an example continuous length of elastomeric laminates 302 from FIGS. 4A, 5A, and 6 taken along line 7-7. It is to be appreciated that different components may be used to construct the elastomeric laminates 302 in accordance with the methods and apparatuses herein. For example, the first and/or second substrates 306, 308 may include nonwovens and/or films, and the elastic material 304 may include one or more elastic elements such as strands, ribbons, or panels.

It is to be appreciated that the metering devices of the apparatus 300 may be configured in various ways. For example, the first metering device 310 shown in FIG. 4A includes a first roller 316 having an outer circumferential surface 318 and rotates about a first axis of rotation 320, and a second roller 322 having an outer circumferential surface 324 and rotates about a second axis of rotation 326. The first roller 316 and the second roller 322 rotate in opposite directions, and the first roller 316 is adjacent the second roller 322 to define a first nip 328 between the first roller 316 and the second roller 322. The first roller 316 rotates such that the outer circumferential surface 318 has a surface speed V1, and the second roller 322 may rotate such that the outer circumferential surface 324 also has the same, or substantially the same, surface speed V1. The second metering 312 device includes a third roller 330 having an outer circumferential surface 332 and rotates about a third axis of rotation 334. The third roller 330 rotates such that the outer circumferential surface 334 has a surface speed V2, wherein V2 is greater than V1. The third metering device 314 includes a fourth roller 336 having an outer circumferential surface 338 and rotates about a fourth axis of rotation 340. The fourth roller 336 may rotate such that the outer circumferential surface 338 has the same, or substantially the same, surface speed V2.

As shown in FIG. 4A, the first substrate 306 includes a first surface 342 and an opposing second surface 344, and the first substrate 306 advances at speed V2 in the machine direction MD from the second roller 322 to the third roller 330. In particular, the first substrate 306 partially wraps around the outer circumferential surface 324 of the second roller 322, such that the first surface 342 of the first substrate 306 travels in an opposing direction to and in contact with the outer circumferential surface 324 of the second roller 322. From the second roller 322, the first substrate 306 advances in the machine direction MD at speed V2 to the third roller 330 where the first substrate 306 partially wraps around the outer circumferential surface 332 of the third roller 330. As such, the second surface 344 of the first substrate 306 travels in the same direction as and in contact with the outer circumferential surface 332 of the third roller 330.

With continued reference to FIG. 4A, the elastic material 304 advances in the machine direction MD through the first nip 328. Upstream of the first nip 328, the elastic material 304 may advance at speed V1 or less. From the first nip 328, the elastic material 304 advances to the third roller 330 where the elastic material 304 is joined with the first surface 342 of the first substrate 306. As shown in FIG. 4A, adhesive 346 may be applied to the elastic material 304 before advancing to the third roller 330. Because the elastic material 304 is advancing at speed V1 at the first nip 328 and is advancing at speed V2 at the third roller 330, wherein V2 is greater than V1, the elastic material 304 is stretched in the machine direction MD between the first nip 328 and the third roller 330. From the third roller 330, the joined elastic material 304 and first substrate 306 advance to the fourth roller 336. As shown in FIG. 4A, the second substrate 308 advances at speed V2 in the machine direction MD to the fourth roller 336. The second substrate 308 includes a first surface 348 and an opposing second surface 350. In particular, the second substrate 308 partially wraps around the outer circumferential surface 338 of the fourth roller 336. As such, the first surface 348 of the second substrate 308 travels in the same direction as and in contact with the outer circumferential surface 338 of the fourth roller 336. While in contact with the fourth roller 336, the advancing second substrate 308 is joined with the elastic material 304 and first substrate 306. In particular, the stretched elastic material 304 and first surface 342 of the first substrate 306 are joined with the second surface 350 of the second substrate 308 at the fourth roller 336 to produce a continuous length of elastomeric laminate 302.

It is to be appreciated that adhesive may also be applied to the first surface 342 of the first substrate 306 before and/or while being joined with the elastic material 304 and/or the second substrate 308. In addition, it is to be appreciated that adhesive may be applied to the second surface 350 of the second substrate 308 before or while being joined with the elastic material 304 and first substrate 306.

Figure 4B:
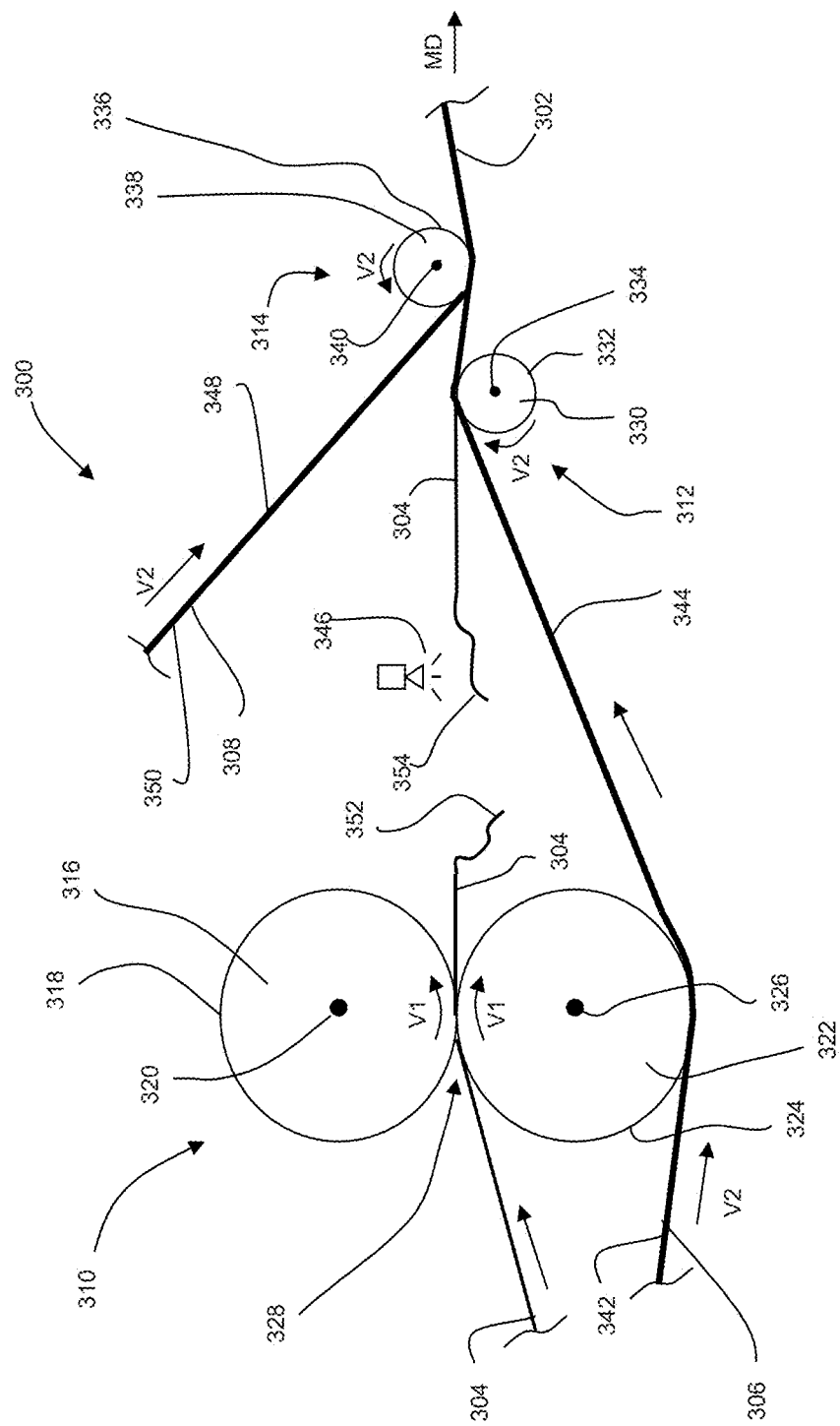
FIG. 4B is a schematic side view of the converting apparatus shown in FIG. 4A showing a broken elastic strand.

As previously mentioned, the elastic material 304 may break while the apparatus 300 is producing an elastomeric laminate 302. As such, the apparatus 300 may be configured to automatically rethread elastic materials 304 that may break during the assembly process. More particularly, the apparatus 300 may be configured to automatically reincorporate upstream end portions of broken elastic materials into the elastomeric laminate being produced without having to stop the production process. For example, FIGS. 4A-4E illustrate a sequence wherein an elastic material 304 breaks and is rethreaded through the apparatus 300 and reincorporated into the elastomeric laminate 302. As described above, FIG. 4A shows the apparatus 300 operating to produce an elastomeric laminate 302 with the elastic material 304 being stretched between the first metering device 310 and the second metering device 312. Adhesive 346 is applied to a length of elastic material 304 while being stretched between the first nip 328 and the third roller 330. FIG. 4B shows a state wherein the elastic material 304 has broken or separated in the machine direction MD between the first nip 328 and the third roller 330, thus creating an upstream end portion 352 and a downstream end portion 354. Because the elastic material was being stretched between the first nip 328 and the third roller 330, the downstream end portion 354 may snap back in a downstream direction toward the third roller 330, and the upstream end portion 352 may snap back in an upstream direction toward the first nip 328.

Figure 4C:
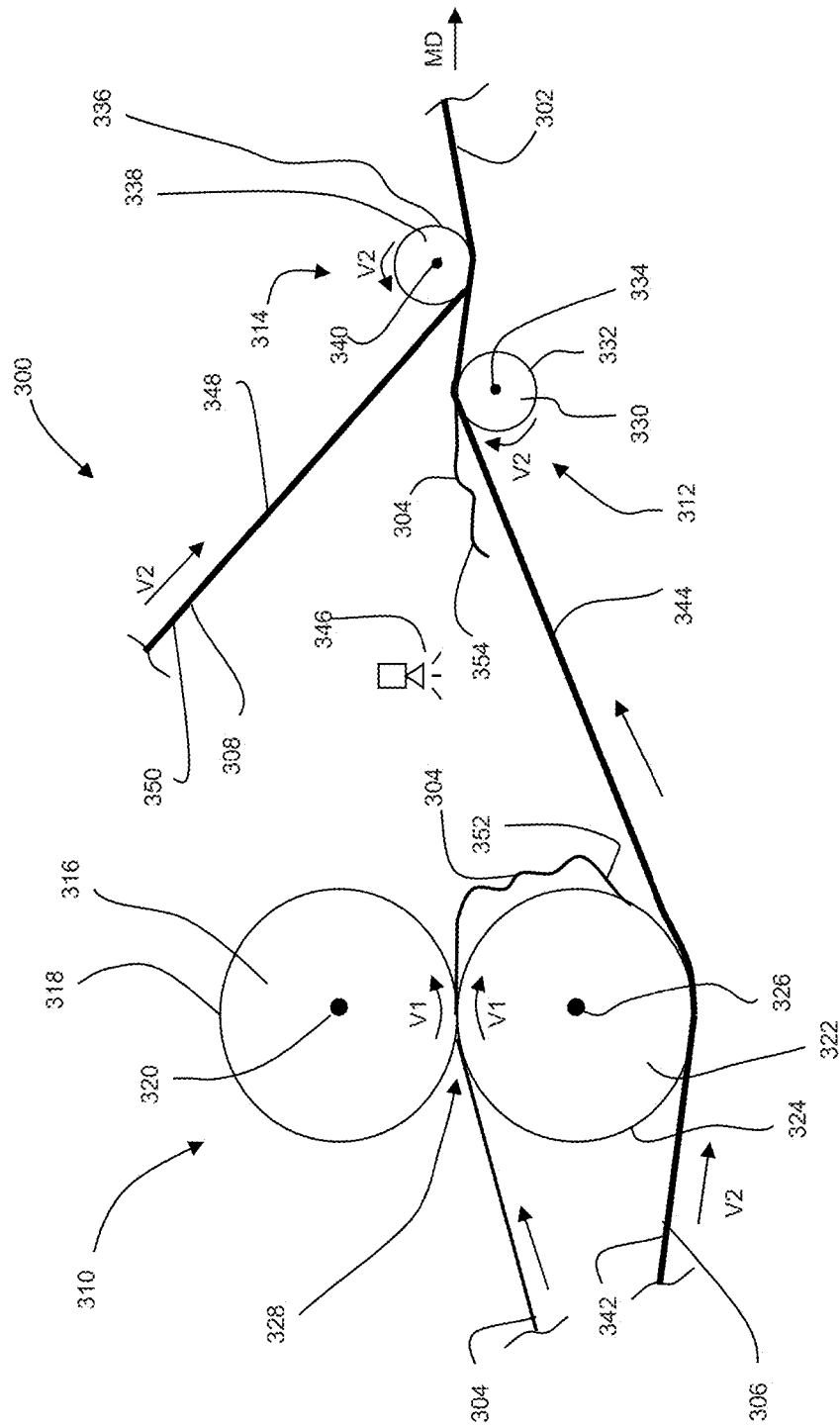
FIG. 4C is a schematic side view of the converting apparatus shown in FIG. 4B showing an upstream end portion of the broken elastic strand joined with the outer circumferential surface of a roller.
Figure 4D:
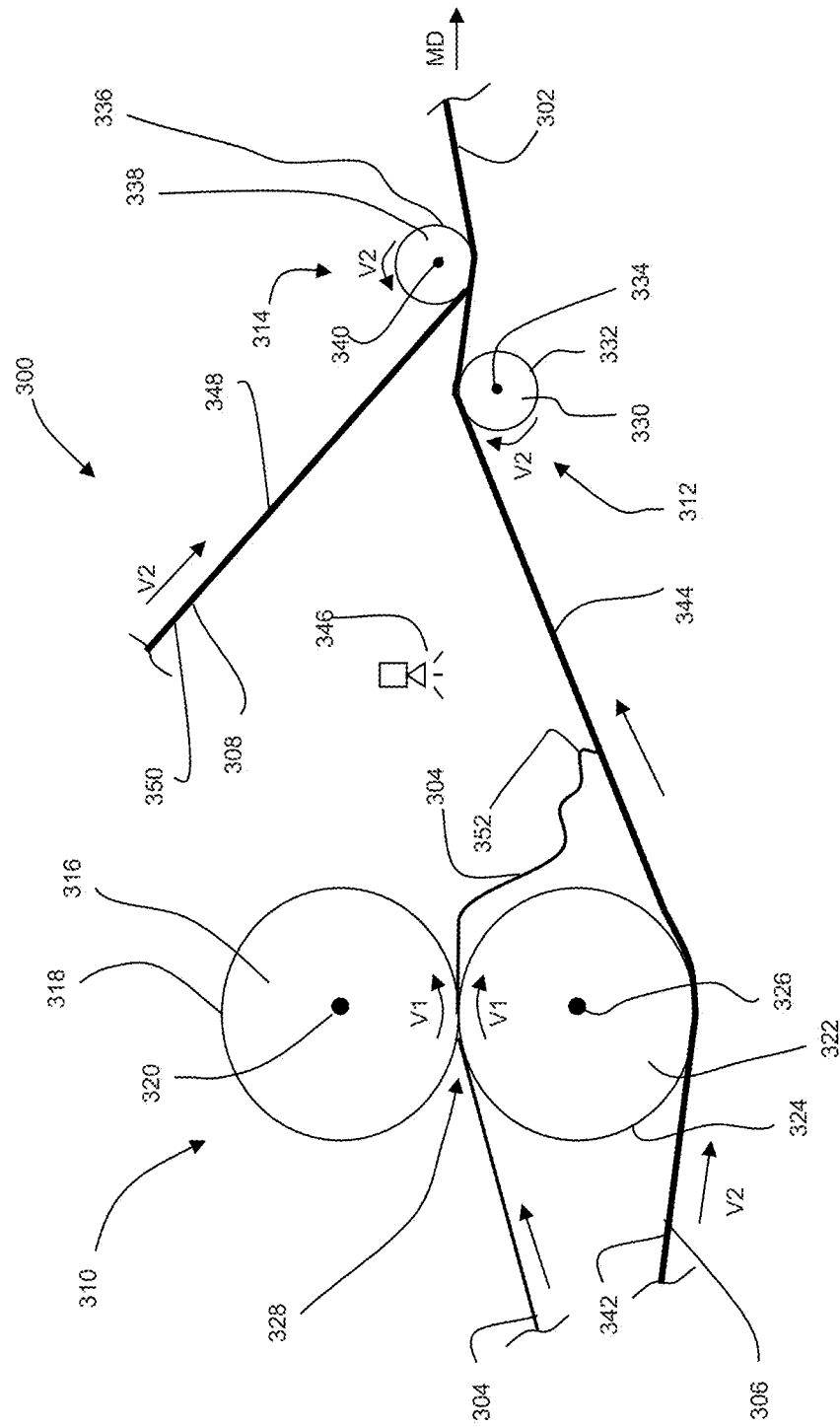
FIG. 4D is a schematic side view of the converting apparatus shown in FIG. 4C showing the upstream end portion of the broken elastic strand after being removed from the roller by the first substrate in contact with the outer circumferential surface of the roller.
Figure 4E:
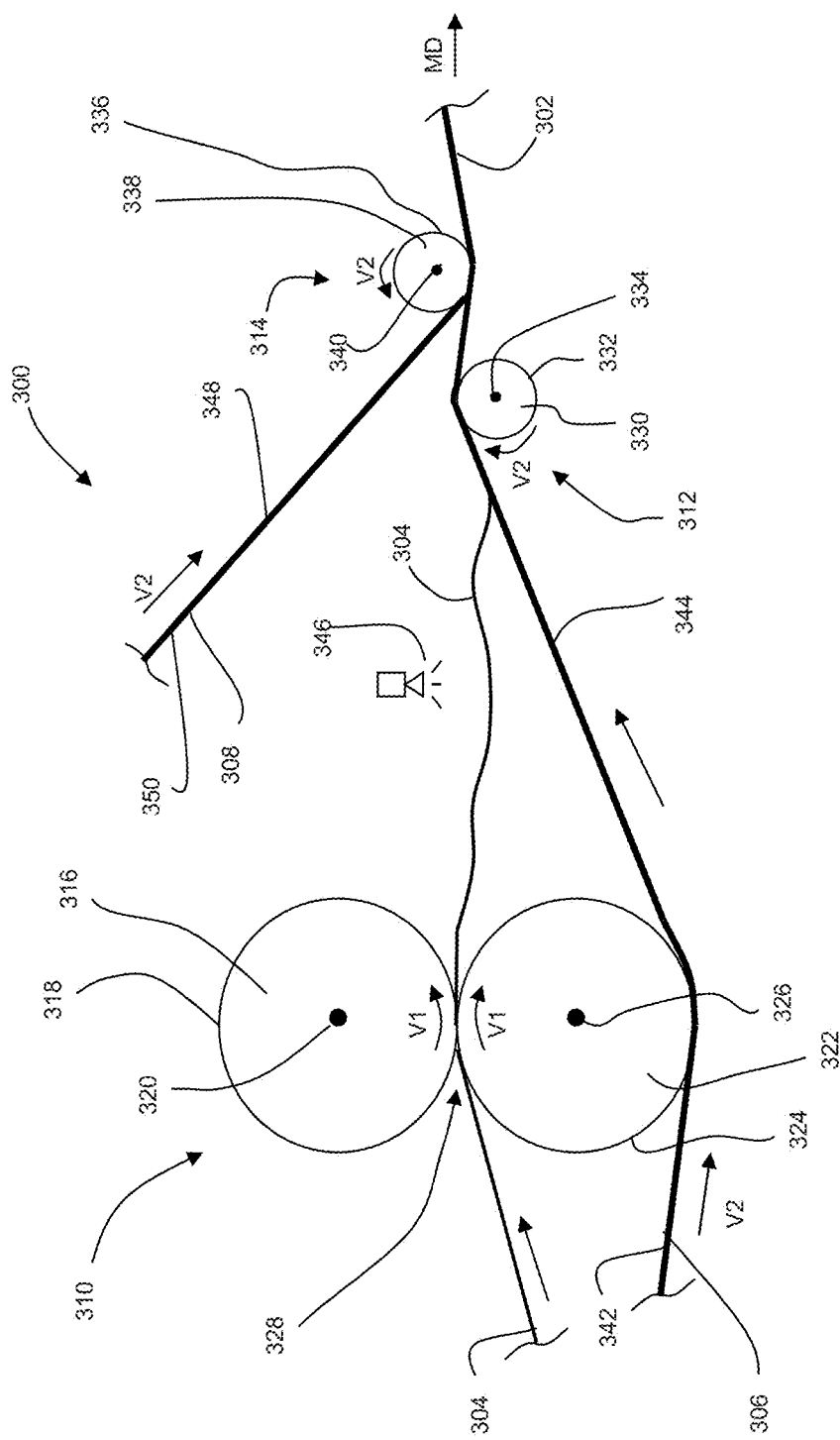
FIG. 4E is a schematic side view of the converting apparatus shown in FIG. 4D showing the upstream end portion of the broken elastic strand being conveyed in the machine direction by the first substrate.
Figure 4A:
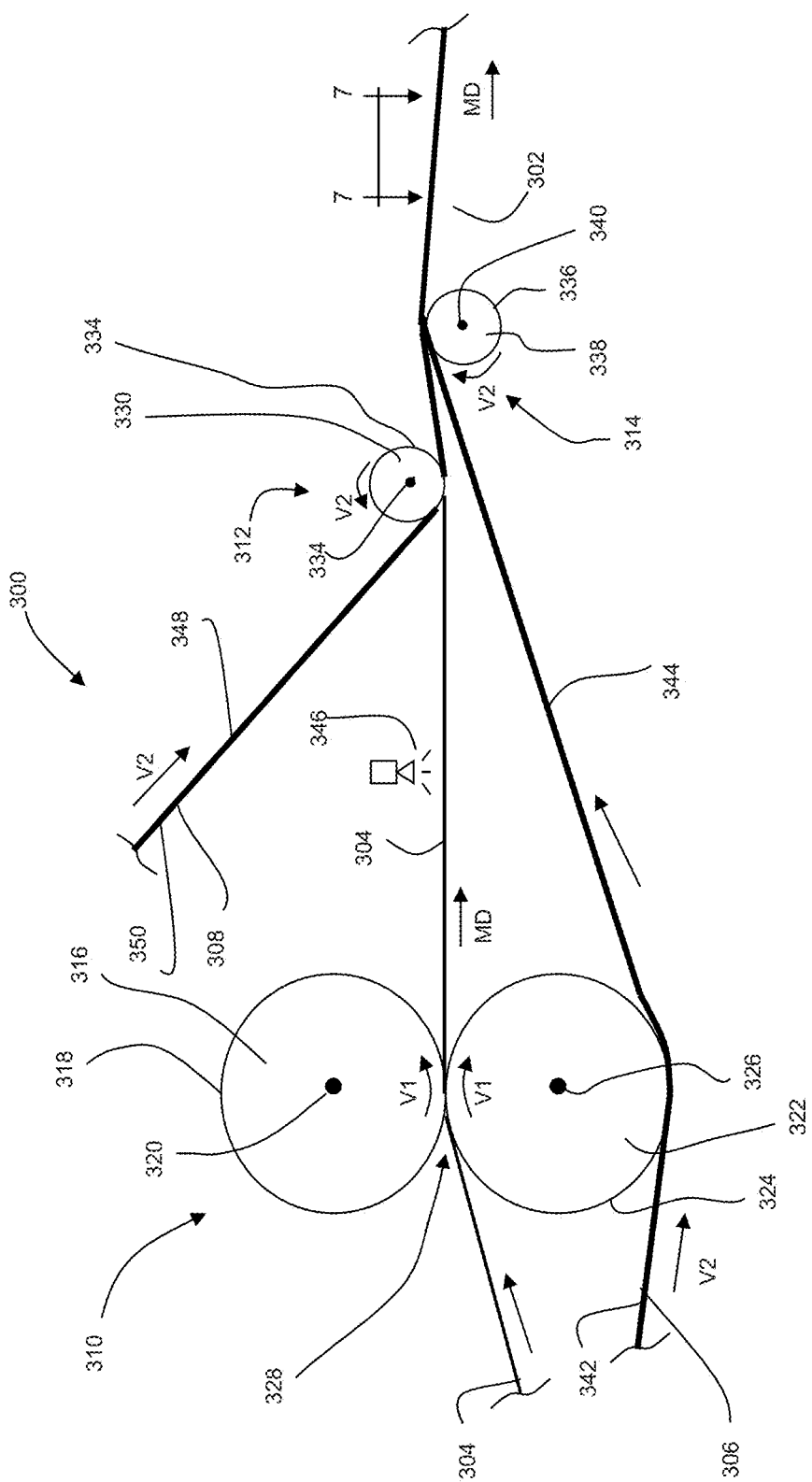
Figure 4A:
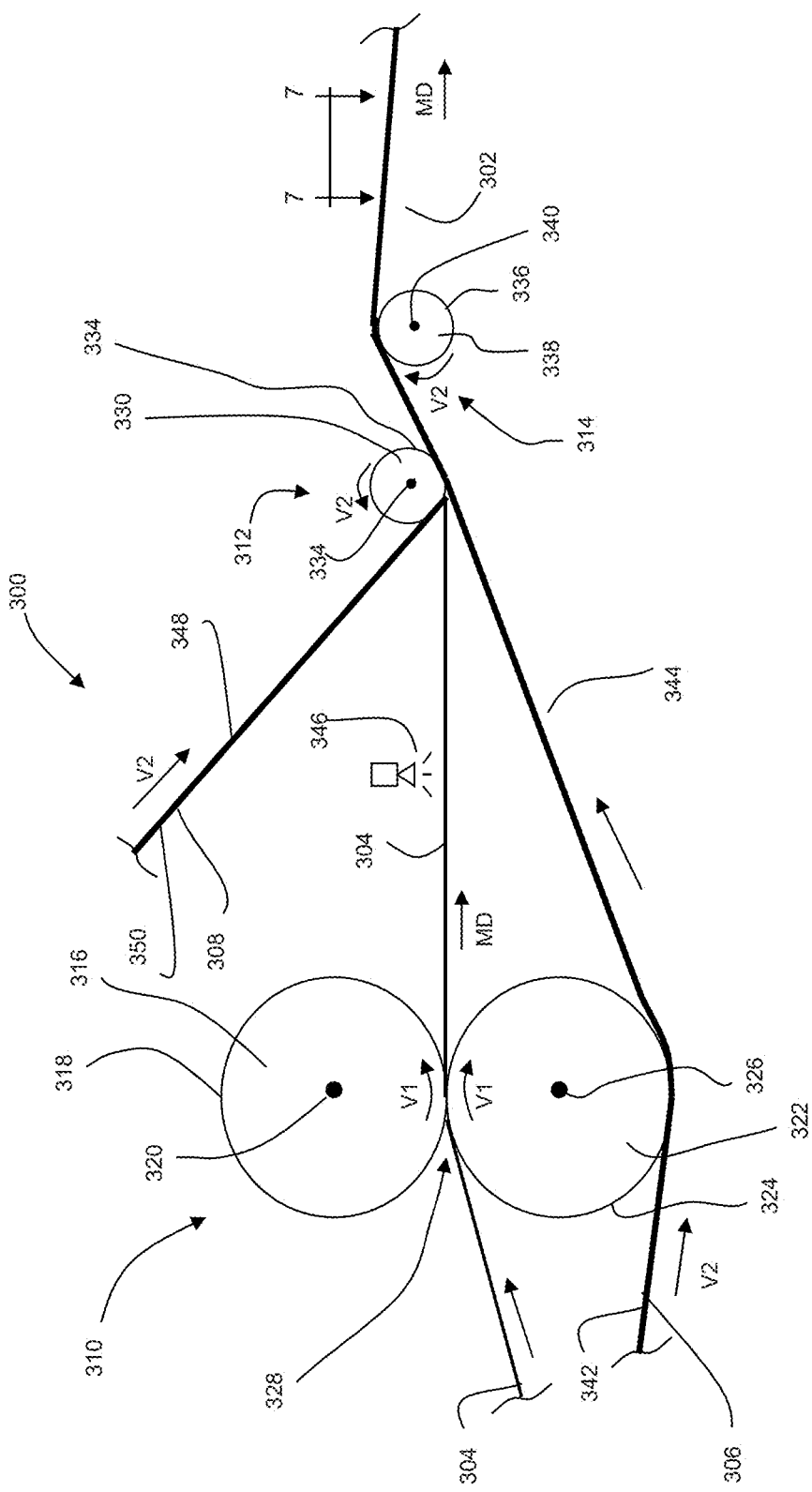

As shown in FIGS. 4C and 4D, the downstream end portion 354 of the broken elastic material 304 continuous to advance in the machine direction MD past the third roller 330 and fourth roller 336 to be incorporated into the elastomeric laminate 302. In some instances, the downstream end portion 354 of the broken elastic material 304 may come into contact with the first surface 342 of the first substrate 306 and may be conveyed by the first substrate 306 past the third and fourth rollers 330, 336. As previously mentioned, the upstream end portion 352 of the broken elastic material 304 may snap back toward the first nip 328. In some instances, the upstream end portion 352 of the elastic material 304 may snap back toward the first nip 328 and become attached with the outer circumferential surface 324 of the second roller 322, such as shown in FIG. 4C. With reference to FIGS. 4C and 4D, the second roller 322 may carry the upstream end portion 352 of the elastic material 304 as the second roller 322 rotates until the upstream end portion 352 is removed from the outer circumferential surface 324 of the second roller 322 by the first surface 342 of the first substrate 306, such as shown in FIG. 4D. As shown in FIGS. 4D and 4E, the upstream end portion 304 of the elastic material 304 may be conveyed by the first substrate 306 in the machine direction MD past the third roller 330 and fourth roller 336 to be incorporated into the elastomeric laminate 302. Once the upstream end portion 352 of the elastic material 304 is conveyed past the third and fourth rollers 330, 336 and reincorporated into the elastomeric laminate 302, the elastic material 304 is restretched between the first nip 328 and third roller 330, such as shown in FIG. 4A.

It is to be appreciated that components of the apparatus 300 may be positioned relative to one another so as help direct the placement of the upstream end portion 352 and downstream end portion 354 of the broken elastic material 304. For example, the apparatus 300 may be configured with the first roller 316 above the second roller 322 and wherein the first substrate 306 is located below the elastic material 304, such as shown in FIGS. 4A-4E. As such, gravity may pull the downstream end portion 354 of the broken elastic material 304 downward and into contact with the first surface 342 of the first substrate 306 before being conveyed by the first substrate 306 to the third roller 330. Similarly, gravity may also pull the upstream end portion 352 of the broken elastic material 304 downward and into contact with the second roller 322 or the first surface 342 of the first substrate 306 before being conveyed by the first substrate 306 to the third roller 330.

It is also to be appreciated that components of the apparatus 300 shown in FIG. 4A, such as the third roller 330 and fourth roller 336, may be arranged in various ways. For example, the apparatus 300 in FIG. 4AA shows an arrangement wherein the second substrate 308 partially wraps around the outer circumferential surface 332 of the third roller 330 and is joined with the elastic material 304. From the second roller 322, the first substrate 306 advances in the machine direction MD to the fourth roller 338 and is joined with the elastic material 304 and second substrate 308. In yet another example, FIG. 4AB shows an arrangement wherein the second substrate 308, elastic material 304, and first substrate 306 are joined together and partially wrap around the outer circumferential surface 332 of the third roller 330 before advancing to the fourth roller 336. In yet another example, the third and fourth rollers 330, 336 may be arranged adjacent to each other so as to define a second nip, such as discussed below with reference to FIG. 5A.

In some instances, the upstream end portion 352 of a broken elastic material 304 may snap back toward the first nip 328 and come into contact with the outer circumferential surface 318 of the first roller 316 or second substrate 308, rather than the second roller 322 or first substrate 306 as discussed above with reference FIGS. 4A-4E. As such, the apparatus 300 may be configured to remove the upstream end portion 352 of broken elastic material 304 from the first roller 316 and/or second substrate 308 and automatically reincorporate the upstream end portion 352 into the elastomeric laminate 302 being produced without having to stop the production process. For example, FIGS. 5A-5E illustrate an embodiment wherein an elastic material 304 breaks; the upstream end portion 352 snaps back in an upstream direction and contacts the first roller 316 and/or the second substrate 308; the upstream end portion 352 is removed from the first roller 316 and/or the second substrate 308; and the upstream end portion 352 is automatically reincorporated into the elastomeric laminate 302.

Figure 5A:
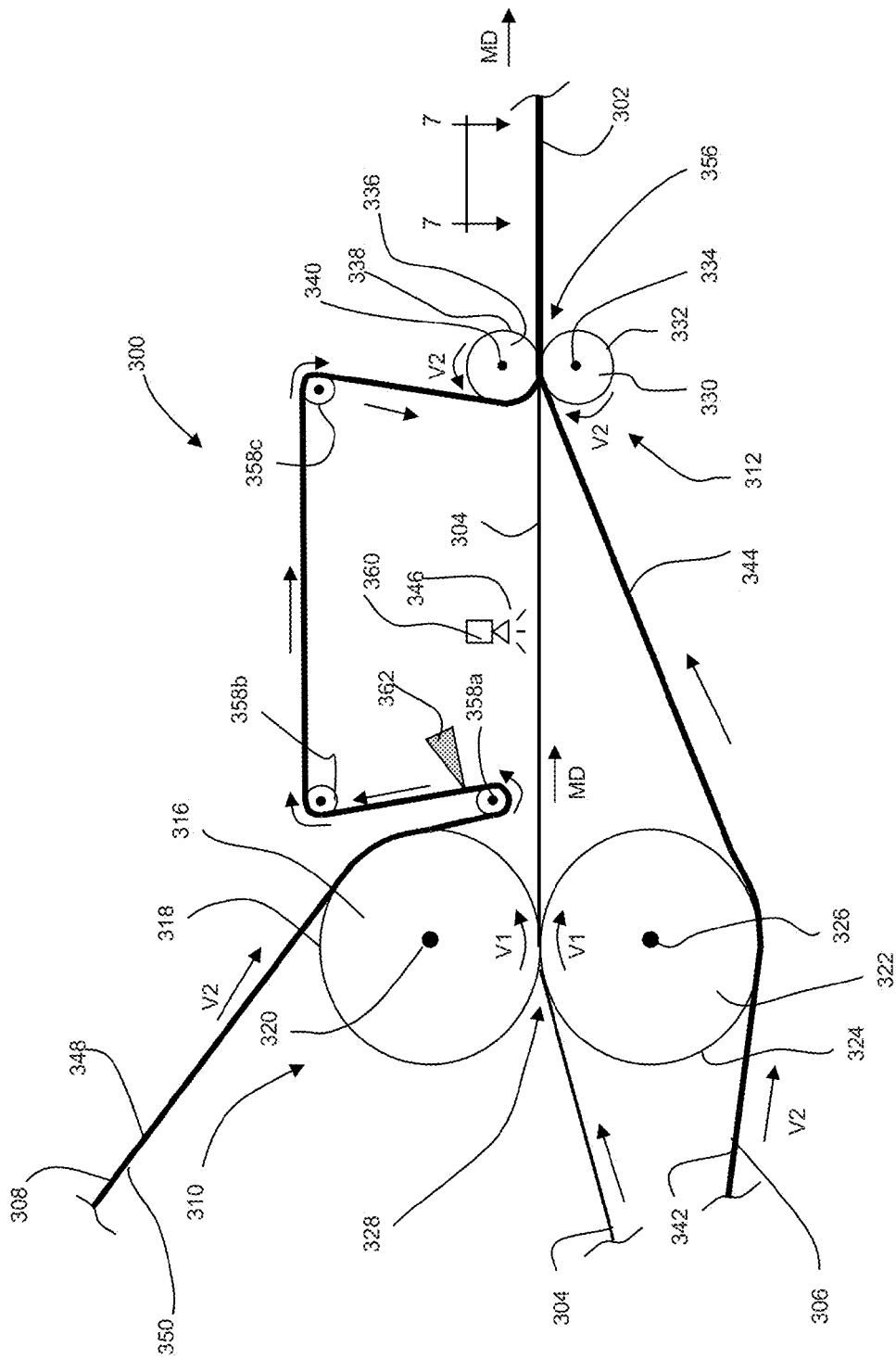
FIG. 5A is a schematic side view of a fourth embodiment of a converting apparatus adapted to manufacture an elastic laminate including a first substrate, a second substrate, and an elastic strand.

As shown in FIG. 5A, the apparatus includes a first metering device 310 and a second metering device 312. The elastic material 304 advances in the machine direction MD from the first metering device 310 to the second metering device 312 and stretch elastic material 304 along the machine direction MD between the first and second metering devices 310, 312. The stretched elastic material 304 is also joined with the first substrate 306 and the second substrate 308 at the second metering device 312 to produce an elastomeric laminate 302.

The first metering device 310 shown in FIG. 5A includes: a first roller 316 having an outer circumferential surface 318 and rotates about a first axis of rotation 320, and a second roller 322 having an outer circumferential surface 324 and rotates about a second axis of rotation 326. The first roller 316 and the second roller 322 rotate in opposite directions, and the first roller 316 is adjacent the second roller 322 to define a first nip 328 between the first roller 316 and the second roller 322. The first roller 316 rotates such that the outer circumferential surface 318 has a surface speed V1, and the second roller 322 may rotate such that the outer circumferential surface 324 also has the same, or substantially the same, surface speed V1. The second metering device includes: a third roller 330 having an outer circumferential surface 332 and rotates about a third axis of rotation 334, and a fourth roller 336 having an outer circumferential surface 338 and rotates about a fourth axis of rotation 340. The third roller 330 and the fourth roller 336 rotate in opposite directions, and the third roller 330 is adjacent the fourth roller 336 to define a second nip 356 between the third roller 330 and the fourth roller 336. The third roller 330 rotates such that the outer circumferential surface 332 has a surface speed V2, and the fourth roller 336 may rotate such that the outer circumferential surface 338 has the same, or substantially the same, surface speed V2, wherein V2 is greater than V1. Although the third and fourth rollers 330, 336 shown in FIG. 5A are arranged to define the second nip 356, it is to be appreciated that the third and fourth rollers may be arranged in a similar configuration as described above with reference to the third and fourth rollers in FIG. 4A.

As shown in FIG. 5A, the first substrate 306 includes a first surface 342 and an opposing second surface 344, and the first substrate 306 advances at speed V2 in the machine direction MD from the second roller 322 to the third roller 330. In particular, the first substrate 306 partially wraps around the outer circumferential surface 324 of the second roller 322, such that the first surface 342 of the first substrate 306 travels in an opposing direction to and in contact with the outer circumferential surface 324 of the second roller 322. From the second roller 322, the first substrate 306 advances in the machine direction MD at speed V2 to the third roller 330 where the first substrate 306 partially wraps around the outer circumferential surface 332 of the third roller 330 and advances through the second nip 356. As such, the second surface 344 of the first substrate 306 travels in the same direction as and in contact with the outer circumferential surface 332 of the third roller 330.

With continued reference to FIG. 5A, the second substrate 308 includes a first surface 348 and an opposing second surface 350, and the second substrate 308 advances at speed V2 in the machine direction MD from the first roller 316 to the fourth roller 336. In particular, the second substrate 308 partially wraps around the outer circumferential surface 318 of the first roller 316, such that the second surface 350 of the second substrate 308 travels in an opposing direction to and in contact with the outer circumferential surface 318 of the first roller 316. From the first roller 316, the second substrate 308 advances in the machine direction MD at speed V2 to the fourth roller 336 where the second substrate 308 partially wraps around the outer circumferential surface 338 of the fourth roller 336 and advances through the second nip 356. As such, the first surface 348 of the second substrate 308 travels in the same direction as and in contact with the outer circumferential surface 338 of the fourth roller 336. As shown in FIG. 5A, the apparatus 300 may also include guide rollers 358a, 358b, 358c to direct the second substrate 308 around components, such as for example adhesive applicators 360, as the second substrate 308 advances from the first roller 316 to the fourth roller 336.

As shown in FIG. 5A, the elastic material 304 advances in the machine direction MD through the first nip 328 to the second nip 356. Upstream of the first nip 328, the elastic material 304 may advance at speed V1 or less. From the first nip 328, the elastic material 304 advances to the second nip 356 where the elastic material 304 is joined with the first and second substrates 306, 308. Because the elastic material 304 is advancing at speed V1 at the first nip 328 and is advancing at speed V2 at the second nip 356, wherein V2 is greater than V1, the elastic material 304 is stretched in the machine direction MD between the first nip 328 and the second nip 356. In turn, the stretched elastic material 304 advances through the second nip 356 between the first and second substrates 306, 308 such that the elastic material is joined with the first surface 342 of the first substrate 306 and the second surface 350 of the second substrate 308 to produce a continuous length of elastomeric laminate 302. As shown in FIG. 5A, adhesive 346 may be applied to the elastic material 304 before advancing to the second nip 356. It is to be appreciated that adhesive may also be applied to the first surface 342 of the first substrate 306 before and/or while being joined with the elastic material 304 and/or the second substrate 308. In addition, it is to be appreciated that adhesive may be applied to the second surface 350 of the second substrate 308 before or while being joined with the elastic material 304 and first substrate 306.

Figure 5B:
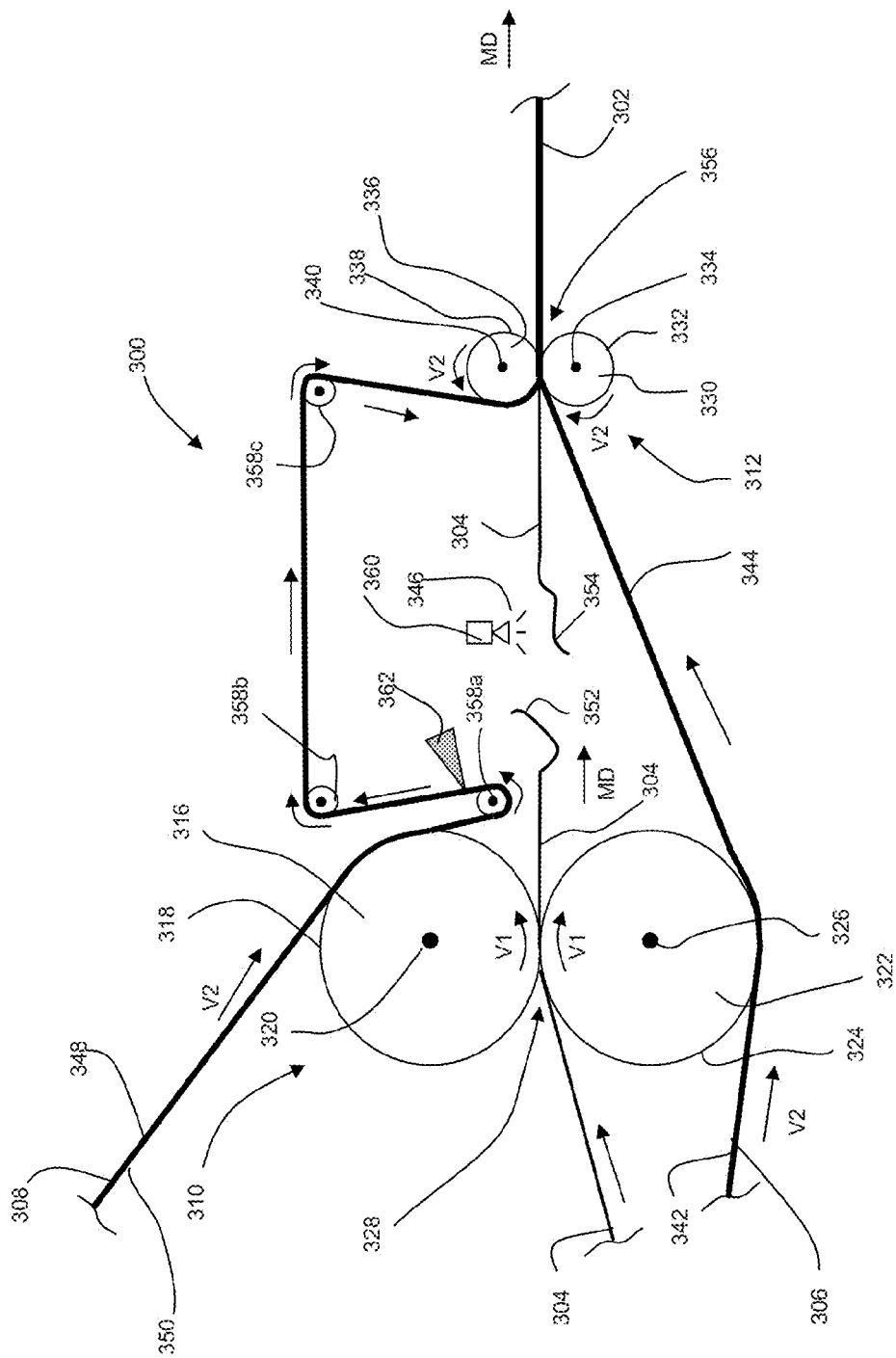
FIG. 5B is a schematic side view of the converting apparatus shown in FIG. 5A showing a broken elastic strand.

As previously mentioned, the elastic material 304 may break while the apparatus 300 is producing an elastomeric laminate 302. FIGS. 5A-5E illustrate a sequence wherein the elastic material 304 breaks and is rethreaded through the apparatus 300 and reincorporated into the elastomeric laminate 302. As described above, FIG. 5A shows the apparatus 300 operating to produce an elastomeric laminate 302 with the elastic material 304 being stretched between the first metering device 310 and the second metering device 312. FIG. 5B shows a state wherein the elastic material 304 has broken or separated in the machine direction MD between the first nip 328 and the second nip 356, thus creating an upstream end portion 352 and a downstream end portion 354. Because the elastic material is being stretched between the first nip and the second nip, the downstream end portion 354 may snap back in a downstream direction toward the second nip 356, and the upstream end portion 352 may snap back in an upstream direction toward the first nip 328.

Figure 5C:
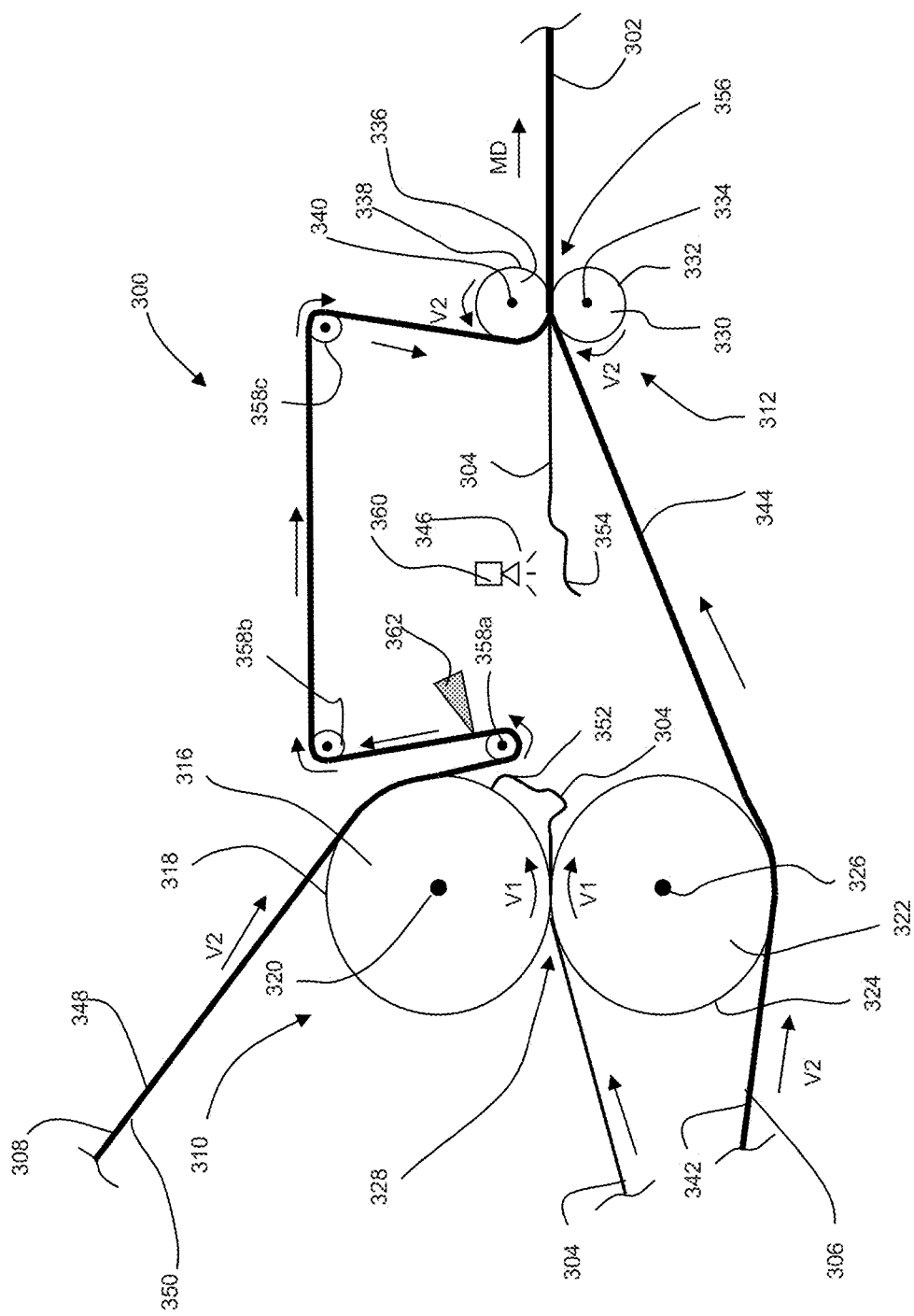
FIG. 5C is a schematic side view of the converting apparatus shown in FIG. 5B showing a broken elastic strand with an upstream end portion of the broken elastic strand joined with the outer circumferential surface of a roller.
Figure 5D:
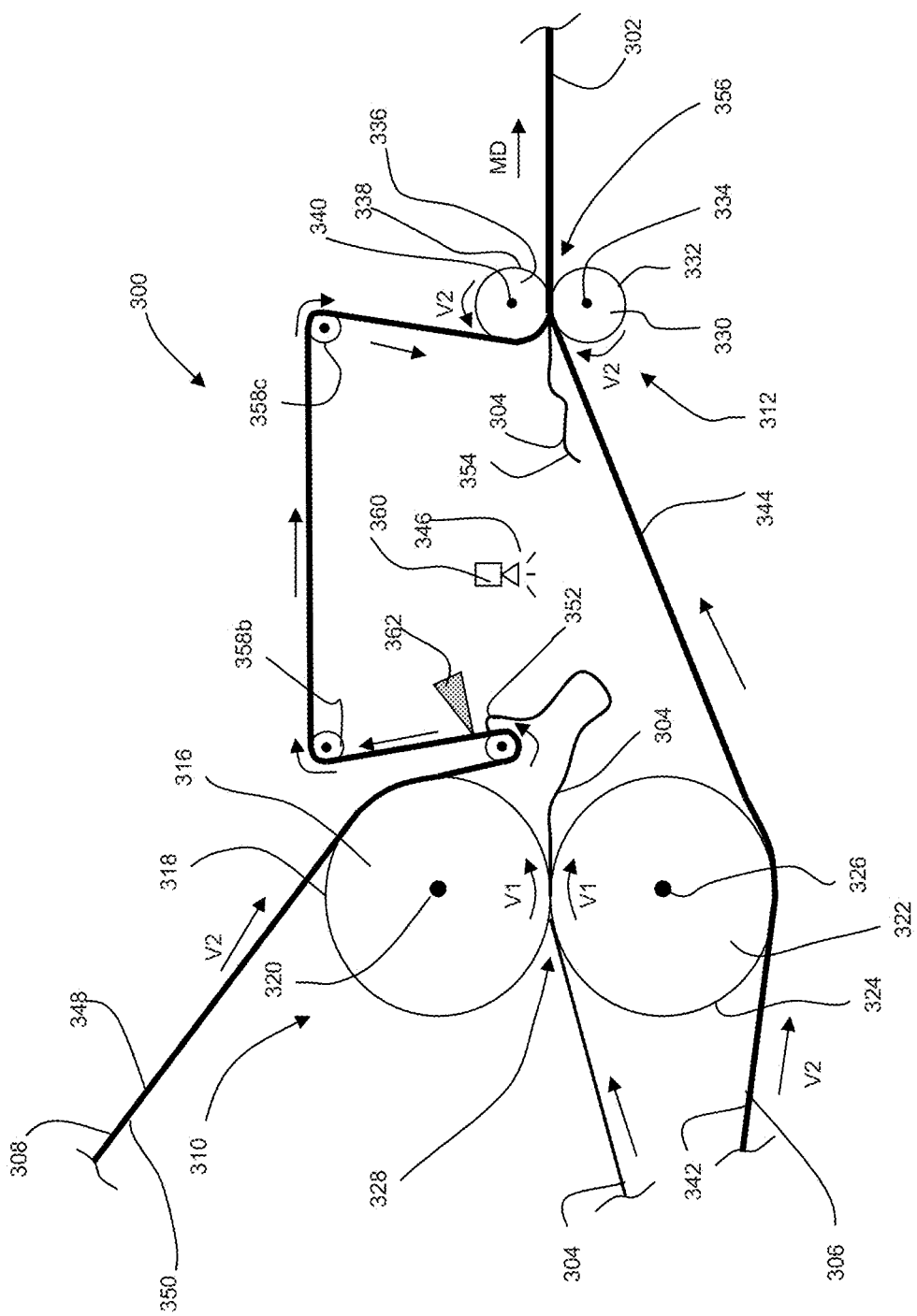
FIG. 5D is a schematic side view of the converting apparatus shown in FIG. 5C showing the upstream end portion of the broken elastic strand after being removed from the roller by the second substrate in contact with the outer circumferential surface of the roller.
Figure 5E:
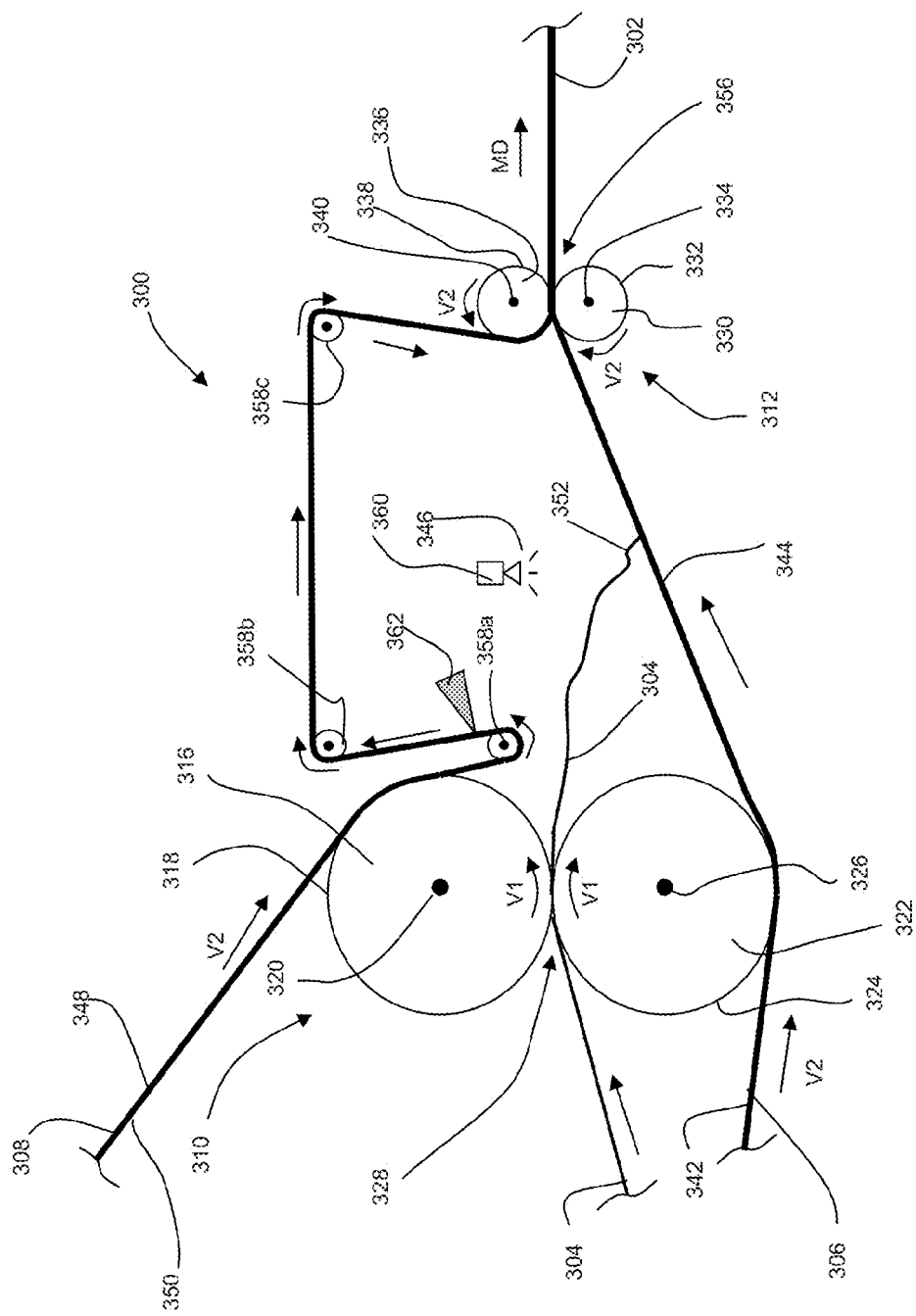
FIG. 5E is a schematic side view of the converting apparatus shown in FIG. 5D showing the upstream end portion of the broken elastic strand after being removed from the second substrate by a scraper member and being conveyed in the machine direction by the first substrate.

As shown in FIGS. 5B-5E, the downstream end portion 354 of the broken elastic material 304 continuous to advance in the machine direction MD through the second nip 356 and is incorporated into the elastomeric laminate 302. In some instances, the downstream end portion 354 of the broken elastic material 304 may come into contact with the first surface 342 of the first substrate 306 and then conveyed by the first substrate 306 through the second nip 356. As previously mentioned, the upstream end portion 352 of the broken elastic material 304 may snap back toward the first nip 328. In some instances, the upstream end portion 352 of the elastic material 304 may snap back toward the first nip 328 and become attached with the outer circumferential surface 318 of the first roller 316, such as shown in FIG. 5C. With reference to FIGS. 5C and 5D, the first roller 316 may carry the upstream end portion 352 as the first roller 316 rotates until the upstream end portion 352 is removed from the outer circumferential surface 318 of the first roller 316 by the second surface 350 of the second substrate 308, such as shown in FIG. 5D. As shown in FIG. 5D, the upstream end portion 352 of the elastic material 304 may then be conveyed by the second substrate 308 to a scraper member 362. The scraper member 362 may be in contact with or adjacent to the second surface 350 of the second substrate 308 such that the scraper member 362 removes the upstream end portion 352 from the second substrate 308. Once removed from the second substrate 308, as shown in FIG. 5E, the upstream end portion 352 of the elastic material 304 may drop down to the first substrate 306. The upstream end portion 352 may then be conveyed by the first substrate 306 in the machine direction MD through the second nip 356 and incorporated into the elastomeric laminate 302. Once the upstream end portion 352 of the elastic material 304 is conveyed past the second nip 356 and reincorporated into the elastomeric laminate 302, the elastic material is restretched between the first nip 328 and second nip 356, such as shown in FIG. 5A.

Although the process sequence shown FIGS. 5A-5E show the upstream end portion 352 of the elastic material 304 coming into contact with the first roller 316 before coming into contact with the second substrate 308 after the elastic member 304 breaks, it is to be appreciated that the upstream end portion may snap back and come into contact with the second substrate 308 without first coming into contact with the first roller 316. In addition, although the embodiment shown in FIGS. 5A-5E illustrate the first roller above the second roller, the fourth roller about the third roller, and the second substrate above the elastic material and first substrate, it is to be appreciated that the apparatus components, substrates, and elastic material may be configured in various different orientations relative to each other. For example, the apparatus may be configured such that the machine direction MD is oriented in upward or downward directions. It is also to be appreciated that the apparatus may be configured in other ways than described above. For example, as shown in FIG. 6, the apparatus of FIG. 5A may be adapted to include a shield 364, instead of a scraper member, that helps to prevent the upstream end portion 352 of a broken elastic material 304 from coming into contact with the first roller 316 and/or second substrate 308. In another example, the shield 364 may include a knife 366, such as a razor blade or serrated edge. The knife 366 may be configured to cut the upstream end portion 352 of a broken elastic material 304 in a situation wherein the upstream end portion 352 becomes attached to the second substrate 308 while traveling from the first roller 316 to the guide roller 358a adjacent the shield 364. It should also be appreciated that the apparatuses 300 described herein could also be adapted to include any one or more of a shield, knife blade, and scraper member. In some instances wherein the upstream end portion 352 of a broken elastic material 304 becomes attached to the second substrate 308 while traveling from the first roller 316 to the guide roller 358a adjacent the shield 364, centrifugal force may cause the upstream end portion 352 to be propelled and separated from the second substrate 308. In yet other configurations, the apparatus may be configured with compressed air and/or vacuum systems to help redirect upstream and/or downstream end portions of broken elastic material 304. In still other configurations, the outer circumferential surfaces of rollers, such as for example, the first roller 316 and/or second roller 322, may be include smooth surfaces, such as for example polished steel or plasma coatings, having relatively low coefficients of friction to help reduce excessive wear and/or necking on the first and/or second substrates 306, 308.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for making an elastomeric laminate, the method comprising the steps of:
    rotating a first roller about a first axis of rotation, the first roller having an outer circumferential surface having a surface speed V1;
    rotating a second roller about a second axis of rotation, the second roller having an outer circumferential surface having a surface speed V1, wherein the first roller and the second roller rotate in opposite directions, and wherein the first roller is adjacent the second roller to define a first nip between the first roller and the second roller;
rotating a third roller about a third axis of rotation, the third roller having an outer circumferential surface having a surface speed V2, wherein V2 is greater than V1;
supplying a first substrate having a first surface and an opposing second surface;
continuously advancing the first substrate at speed V2 in a machine direction, wherein the first surface of the first substrate travels in an opposing direction to and in contact with the outer circumferential surface of the second roller, and wherein the second surface of the first substrate travels in the same direction as and in contact with the outer circumferential surface of the third roller;
stretching an elastic material in the machine direction by advancing the elastic material through the first nip to the third roller; and
joining the elastic material with the first surface of the first substrate while the second surface of the first substrate contacts the outer circumferential surface of the third roller.

2. The method of claim 1, further comprising the step of applying adhesive to the elastic material subsequent to advancing through the first nip and before joining the elastic material with the first surface of the first substrate.

3. The method of claim 1, further comprising the steps of:
supplying a second substrate having a first surface and an opposing second surface; and
joining second surface of the second substrate with the elastic material and the first surface of the first substrate.

4. The method of claim 3, further comprising the step of:
rotating a fourth roller about a fourth axis of rotation, the fourth roller having an outer circumferential surface having a surface speed V2, and wherein the fourth roller is adjacent the third roller to define a second nip between the third roller and the fourth roller; and
advancing the first substrate, the second substrate, and the elastic material through the second nip.

5. The method of claim 3, further comprising the steps of:
rotating a fourth roller about a fourth axis of rotation, the fourth roller having an outer circumferential surface having a surface speed V2;
continuously advancing the second substrate at speed V2 in the machine direction, wherein the first surface of the second substrate travels in the same direction as and in contact with the outer circumferential surface of the fourth roller; and
joining second surface of the second substrate with elastic material and the first surface of the first substrate subsequent to joining the elastic material with the first surface of the first substrate.

6. The method of claim 3, further comprising the step of:
continuously advancing the second substrate at speed V2 in the machine direction, wherein the second surface of the second substrate travels in an opposing direction to and in contact with the outer circumferential surface of the first roller.

7. The method of claim 6, further comprising the step of providing a scraper member in contact with the second surface of the second substrate.

8. The method of claim 3, further comprising the step of providing a shield adjacent the first nip between the elastic material and the second surface of the second substrate.

9. The method of claim 1, wherein the first substrate comprises a nonwoven.

10. The method of claim 1, wherein the first surface of the first substrate is below the elastic material.

11. The method of claim 1, wherein the elastic material comprises an elastic strand.

* * * * *